(12) United States Patent
Katsushima et al.

(10) Patent No.: US 10,888,293 B2
(45) Date of Patent: Jan. 12, 2021

(54) RADIOGRAPHIC IMAGE CAPTURING SYSTEM AND METHOD FOR GENERATING AND DISPLAYING COMBINED IMAGE FOR CHECK

(71) Applicant: Konica Minolta, Inc., Tokyo (JP)

(72) Inventors: Kazuhiko Katsushima, Hino (JP); Wataru Matsushita, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 56 days.

(21) Appl. No.: 16/072,714

(22) PCT Filed: Dec. 1, 2016

(86) PCT No.: PCT/JP2016/085694
§ 371 (c)(1),
(2) Date: Jul. 25, 2018

(87) PCT Pub. No.: WO2017/130561
PCT Pub. Date: Aug. 3, 2017

(65) Prior Publication Data
US 2019/0029627 A1    Jan. 31, 2019

(30) Foreign Application Priority Data

Jan. 28, 2016    (JP) ................................. 2016-014286

(51) Int. Cl.
*A61B 6/00*       (2006.01)
*G06T 7/30*       (2017.01)
(Continued)

(52) U.S. Cl.
CPC .......... *A61B 6/5241* (2013.01); *A61B 6/4233* (2013.01); *A61B 6/4266* (2013.01);
(Continued)

(58) Field of Classification Search
CPC ........................... A61B 6/4266; A61B 6/5241
See application file for complete search history.

(56) References Cited

U.S. PATENT DOCUMENTS

2016/0220211 A1*    8/2016    Yamada ............... A61B 6/5229

FOREIGN PATENT DOCUMENTS

JP    2011224338 A    11/2011
JP    2012045159 A    3/2012
(Continued)

OTHER PUBLICATIONS

Written Opinion of the International Searching Authority dated Jan. 31, 2017 from corresponding International Application No. PCT/JP2016/085694 and English translation.
(Continued)

*Primary Examiner* — Dani Fox
(74) *Attorney, Agent, or Firm* — Lucas & Mercanti, LLP

(57) ABSTRACT

Provided is a flat panel detection system which is capable of appropriately shortening the time from irradiation with radiation for long length imaging to the display of a stitched image as well as the time taken for photography. Provided is a flat panel detection system 50, comprising: flat panel detectors P1-P3 which respectively read out, from a plurality of radiation detection elements 7, signal values D based on dosages of irradiated radiation; a display unit Ca; and an image generating unit C, 22 which generates a stitched image p. Before generating the stitched image p for output, the image generating unit C, 22 generates stitched images for verification ppre_raw, ppre_cor, by substituting an abbreviated process for any of the processes of a) generating radiological images p1-p3, b) image processing upon the radiological images p1-p3, or c) generating the stitched image p for output, and carrying out said process, and causes
(Continued)

the display unit Ca to display the generated stitched images for verification ppre_raw, ppre_cor.

14 Claims, 17 Drawing Sheets

(51) Int. Cl.
*G06T 5/50* (2006.01)
*H04N 5/32* (2006.01)
*H05G 1/60* (2006.01)

(52) U.S. Cl.
CPC ............... *A61B 6/548* (2013.01); *G06T 5/50* (2013.01); *G06T 7/30* (2017.01); *H04N 5/32* (2013.01); *A61B 6/465* (2013.01); *G06T 2200/32* (2013.01); *G06T 2207/10116* (2013.01); *G06T 2207/10124* (2013.01); *G06T 2207/20212* (2013.01); *G06T 2207/30008* (2013.01); *H05G 1/60* (2013.01)

(56) References Cited

FOREIGN PATENT DOCUMENTS

| | | |
|---|---|---|
| JP | 2013-111366 A | 6/2013 |
| JP | 2013226243 A | 11/2013 |
| JP | 2016-140510 A | 8/2016 |
| JP | 2016140513 A | 8/2016 |

OTHER PUBLICATIONS

International Search Report dated Jan. 31, 2017 for PCT/JP2016/085694 and English translation.

JPO, Office Action issued in the related Japanese Application No. 2017-563720, dated Apr. 21, 2020, with English translation.

\* cited by examiner

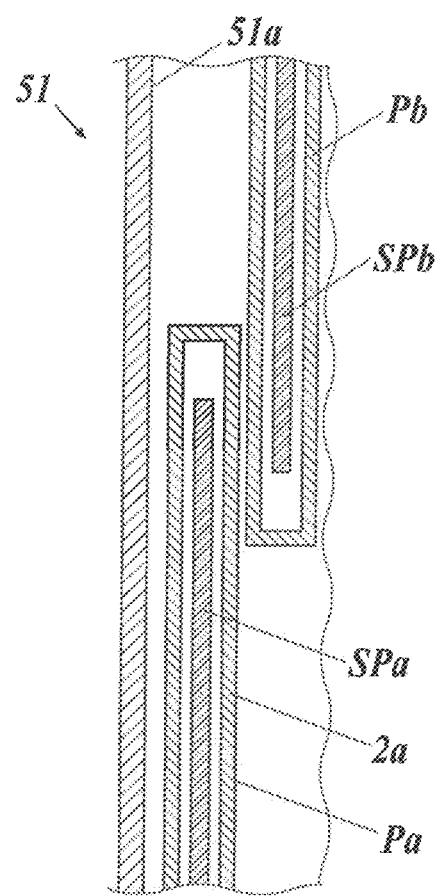

FIG.6

|     | 1       | 2       | 3       | 4       | 5       |      |
|-----|---------|---------|---------|---------|---------|------|
| L1  | D(1,1)  | D(1,2)  | D(1,3)  | D(1,4)  | D(1,5)  | ---  |
| L2  | D(2,1)  | D(2,2)  | D(2,3)  | D(2,4)  | D(2,5)  | ---  |
| L3  | D(3,1)  | D(3,2)  | D(3,3)  | D(3,4)  | D(3,5)  | ---  |
| L4  | D(4,1)  | D(4,2)  | D(4,3)  | D(4,4)  | D(4,5)  | ---  |
| L5  | D(5,1)  | D(5,2)  | D(5,3)  | D(5,4)  | D(5,5)  | ---  |
| L6  | D(6,1)  | D(6,2)  | D(6,3)  | D(6,4)  | D(6,5)  | ---  |
| L7  | D(7,1)  | D(7,2)  | D(7,3)  | D(7,4)  | D(7,5)  | ---  |
| L8  | D(8,1)  | D(8,2)  | D(8,3)  | D(8,4)  | D(8,5)  | ---  |
| L9  | D(9,1)  | D(9,2)  | D(9,3)  | D(9,4)  | D(9,5)  | ---  |
| L10 | D(10,1) | D(10,2) | D(10,3) | D(10,4) | D(10,5) | ---  |
| L11 | D(11,1) | D(11,2) | D(11,3) | D(11,4) | D(11,5) | ---  |
| L12 | D(12,1) | D(12,2) | D(12,3) | D(12,4) | D(12,5) | ---  |

RADIOGRAPHIC IMAGE CAPTURING SYSTEM AND METHOD FOR GENERATING AND DISPLAYING COMBINED IMAGE FOR CHECK

CROSS REFERENCE TO RELATED APPLICATION

This Application is a 371 of PCT/JP2016/085694 filed on Dec. 1, 2016, which, in turn, claimed the priority of Japanese Patent Application No. 2016-014286 filed on Jan. 28, 2016, both applications are incorporated herein by reference.

TECHNICAL FIELD

The present invention relates to a radiographic image capturing system and a method for generating and displaying a combined image for check, especially a radiographic image capturing system and a method for generating and displaying a combined image for check capable of capturing a long image.

BACKGROUND ART

When a subject is captured by using a radiographic image capturing device (Flat Panel Detector) which has a plurality of two-dimensionally arranged (in a matrix) radiation detectors generating electrical charges according to doses of emitted radiation, a capturing site cannot be fit in a size of a single radiographic image capturing device in some cases if the capturing site has a broad capturing area such as a full spine or a full leg of a patient.

Conventionally, in such cases, a plurality of radiographic images has been obtained by loading a radiographic image capturing device P in a holder 101 of a capturing stand 100, and emitting radiation a plurality of times from a radiation generator 102 to the capturing site of the patient which is a subject H while moving the radiographic image capturing device P from the upper side to the lower side, as shown in FIG. 14, for example. By combining these radiographic images p1 to p3 (see FIG. 15A), there has been generated a radiographic image p (see FIG. 15B. FIGS. 15A and 15B show a case where the capturing site is a full leg (right leg)) capturing the capturing site such as a full spine or a full leg (for example, see Patent Document 1).

The capturing method of capturing the capturing site (for example, a full spine or a full leg) which is not fit in the size of a single radiographic image capturing device by dividing the capturing site into a plurality of radiographic images, and generating a radiographic image (hereinafter, referred to as a combined image) by combining these radiographic images as described above is referred to as long image capturing. The long image capturing which is performed by moving the radiographic image capturing device P as shown in FIG. 14 is referred to as moving type long image capturing in some cases.

FIG. 14 shows a case where the long image capturing is performed by arranging a screen 103 which has an opening in front of the radiation generator 102, moving the screen 103 in a vertical direction to move the opening, and changing the emitting direction of radiation so that the radiation is emitted to the radiographic image capturing device P moving in the vertical direction.

However, though not shown in the drawings, there are other cases such as a case where the long image capturing is performed while moving the radiation generator 102 in the vertical direction similarly to the radiographic image capturing device P moving in the vertical direction and a case where the long image capturing is performed by causing the radiation generator 102 to perform a nodding movement to change the emitting direction of radiation so that the radiation is emitted to the radiographic image capturing device P moving in the vertical direction, for example.

On the other hand, in recent years, as shown in FIG. 16, for example, there has been developed, as a method for performing long image capturing, a method of performing the long image capturing by loading a plurality of aligned radiographic image capturing devices P1 to P3 in the holder 101 of the capturing stand 100 in advance, and emitting radiation only a single time (that is by one shot) to a plurality of radiographic image capturing devices P1 to P3 via the capturing site of the patient which is a subject H from the radiation generator 102 (for example, see Patent Documents 2 and 3). Hereinafter, such long image capturing is referred to as one-shot long image capturing in some cases.

Though the same can be said for the case of conventional long image capturing (see FIG. 14), in addition to a case where the long image capturing is performed in an upright position as shown in FIG. 16, there is a case of performing long image capturing by loading a plurality of radiographic image capturing devices P1 to P3 aligned in a horizontal direction into the holder 101 and emitting the radiation from above in a state in which the patient which is the subject H lies (that is, in a recumbent state) on a top panel 104 arranged above them as shown in FIG. 17, for example.

PRIOR ART DOCUMENTS

Patent Documents

Patent Document 1: Japanese Patent Application Laid Open Publication No. 2013-226243
Patent Document 2: Japanese Patent Application Laid Open Publication No. 2011-224338
Patent Document 3: Japanese Patent Application Laid Open Publication No. 2012-045159

DISCLOSURE OF THE INVENTION

Problems to be Solved by the Invention

In a case of simple radiography (that is, radiography of capturing a single radiographic image by once emitting radiation to a single radiographic image capturing device P), there may be a configuration in which signal values read out from a plurality of radiation detectors of the radiographic image capturing device P are transferred to a console, the console generates a radiographic image on the basis of the signal values and displays the radiographic image on a display screen, and an operator such as a radiologist looks at the displayed radiographic image to determine whether retake is necessary and the like.

However, if this configuration is applied to the above long image capturing, each of the radiographic images p1 to p3 (see FIG. 15A) is generated by the console on the basis of the signal values read out by the radiographic image capturing device P, image processing is performed to each of the radiographic images, then the radiographic images are combined to generate a combined image p (see FIG. 15B) and the generated image is displayed on the display screen, and thus, the time required from the emission of radiation for long image capturing to the generation of combined image p and displaying of the combined image p on the display screen is approximately tens of seconds, which is very long.

Thus, since the operator such as a radiologist needs to wait for a long time from emission of radiation until the operator becomes able to look at the combined image p to determine whether retake is necessary, the operator cannot promptly proceed to next capturing (for example, calling of the next patient) or next processing, thus lowering the work efficiency. The patient which is the capturing target of the long image capturing needs to wait for a long time until the patient is released by the determination that retake is not necessary, and thus, the binding time of the patient is long.

The editing processing such as adjustment of the density and the contrast for the combined image p can be performed only after the combined image p is generated as described above. Thus, the operator such as a radiologist can start the editing processing for the combined image p only after the operator waits for approximately tens of seconds from the above-described emission of radiation for the long image capturing to the generation of the combined image p, which has caused a problem of a very long time (that is, capturing time) from when the capturing is performed to when the combined image p is generated and subjected to the editing processing and the capturing is finished.

The present invention has been considered in view of the above problems, and an object of the present invention is to provide a radiographic image capturing system and a method for generating and displaying a combined image for check which can accurately shorten the time from emission of radiation for the long image capturing to displaying of the combined image and the capturing time.

Means for Solving the Problem

In order to achieve at least one of the above objects, a radiographic image capturing system reflecting an aspect of the present invention includes: a radiographic image capturing device which reads signal values corresponding to doses of emitted radiation from a plurality of respective radiation detectors; a display; and an image generator which generates a plurality of radiographic images based on the signal values read by the radiographic image capturing device, and generates a combined image by combining the generated plurality of radiographic images, and before the combined image for output is generated, the image generator generates a combined image for check by replacing processing among generation of the radiographic images, image processing to the radiographic images and generation of the combined image for output with simplified processing and performing the simplified processing, and the image generator causes the generated combined image for check to be displayed on the display.

In order to achieve at least one of the above objects, a method for generating and displaying a combined image for check reflecting another aspect of the present invention is a method for generating and displaying a combined image for check of generating a plurality of radiographic images based on signal values read from a plurality of respective radiation detectors in a radiographic image capturing device, and combining the generated plurality of radiographic images to generate and display the combined image for check, the method including replacing processing among generation of the radiographic images, image processing to the radiographic images and generation of a combined image with processing which is more simplified than processing performed when the combined image for output is generated, and performing the simplified processing to generate and display the combined image for check.

Effects of the Invention

According to the radiographic image capturing system and the method for generating and displaying the combined image for check in a form as in the present invention, it is possible to accurately shorten the time from emission of radiation for the long image capturing to displaying of the combined image and the capturing time.

BRIEF DESCRIPTION OF DRAWINGS

FIG. 4 This is an enlarged sectional view showing a portion where radiographic image capturing devices overlap in a front-back direction in a holder of a capturing stand.

FIG. 6 This is a view explaining an example of how to extract a signal value for check.

EMBODIMENTS FOR CARRYING OUT THE INVENTION

Hereinafter, an embodiment of a radiographic image capturing system and a method for generating and displaying a combined image for check according to the present invention will be described with reference to the drawings.

Though the description below is made for a case where one-shot long image capturing is performed by loading three radiographic image capturing devices into a holder of a capturing stand for long image capturing so as to be aligned, the present invention is not limited to this case (also not limited to a case of three radiographic image capturing devices), and is also applied to a case of moving type long image capturing (see FIG. 14), for example.

Figure 17:
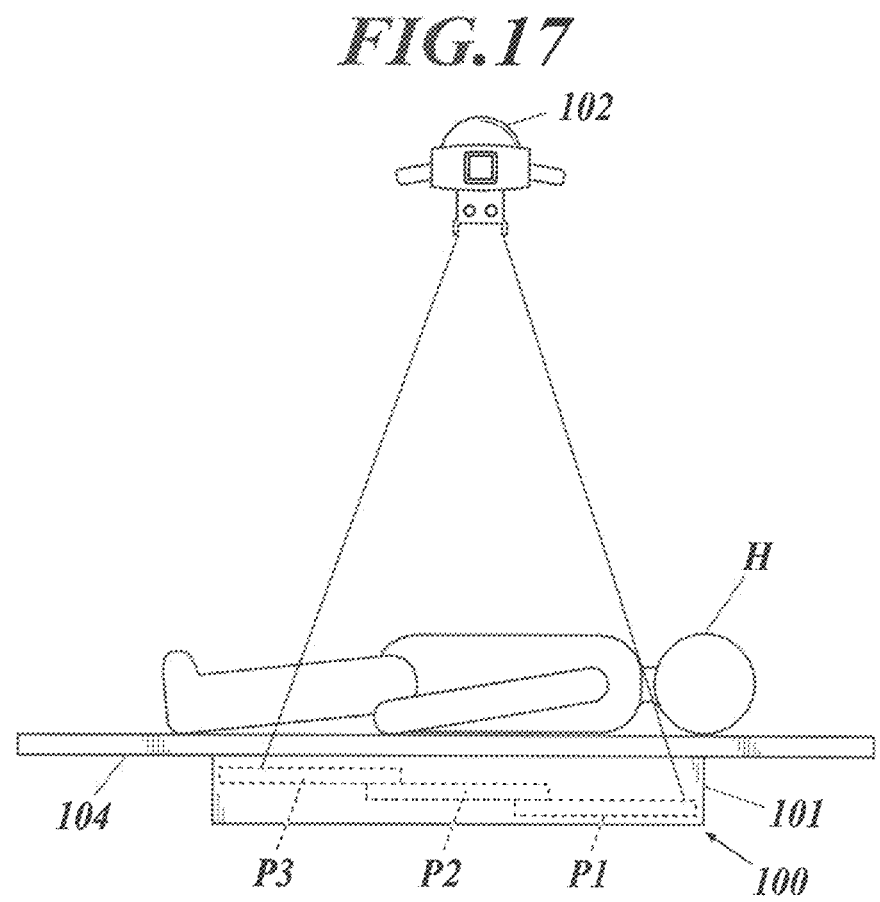
FIG. 17 This is a view showing a configuration example in a case where one-shot long image capturing is performed in a recumbent state.

Though the description below is made for a case where the capturing stand for one-shot long image capturing to load the three radiographic image capturing devices is a capturing stand for upright capturing, the capturing stand for one-shot long image capturing may be a capturing stand for recumbent capturing as shown in FIG. 17.

[Configuration Example of Radiographic Image Capturing System]

Figure 1:
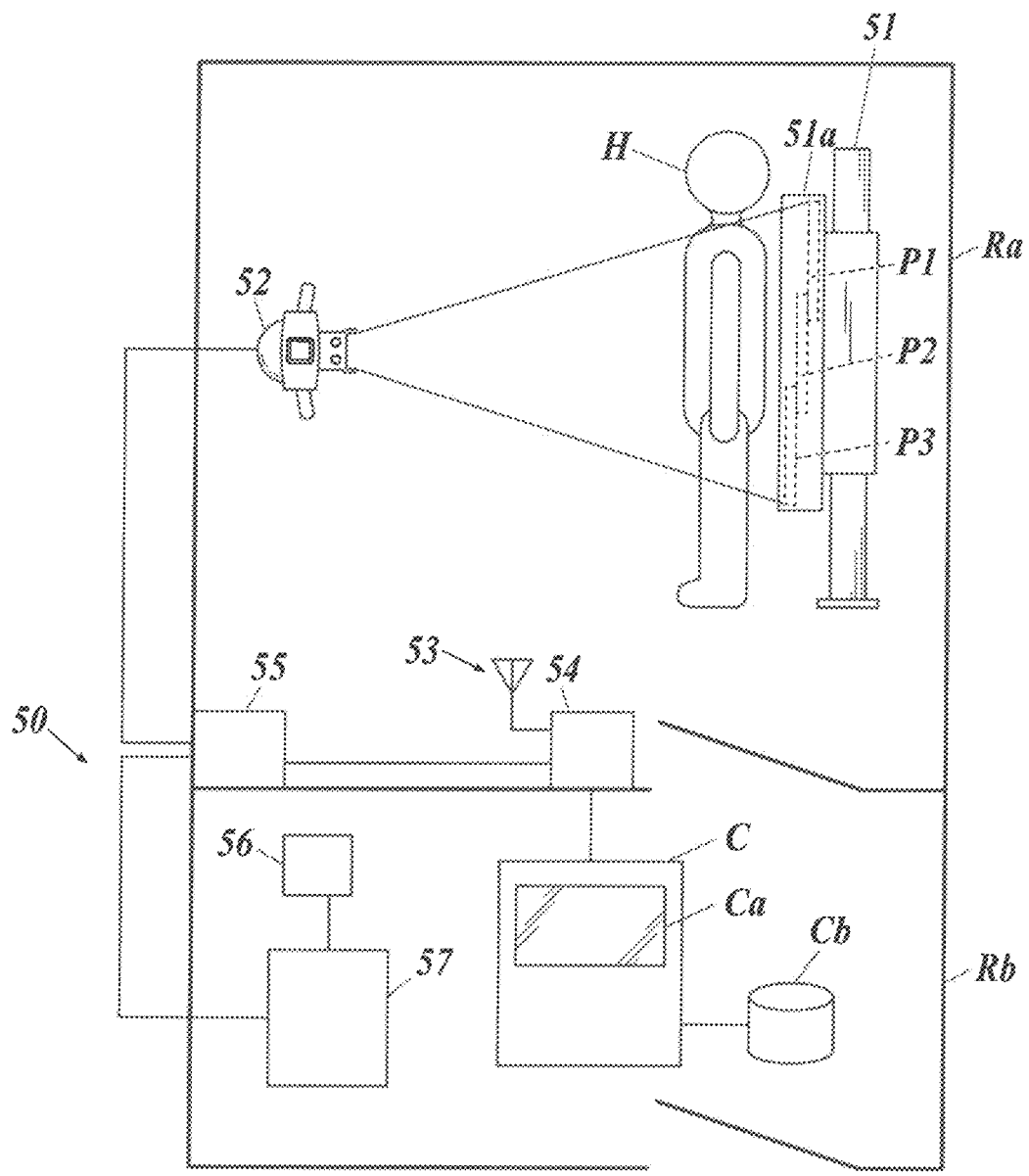
FIG. 1 This is a view showing a configuration example of a radiographic image capturing system according to the embodiment.

FIG. 1 is a view showing a configuration example of a radiographic image capturing system 50 according to the embodiment (that is, configuration example of a case where one-shot long image capturing is performed as described above). As shown in FIG. 1, in the embodiment, there is provided, in a capturing room Ra, a capturing stand 51 for one-shot long image capturing in which a plurality of radiographic image capturing devices P1 to P3 can be loaded in order to perform long image capturing. The capturing stand 51 is configured so that the plurality of radiographic image capturing devices P1 to P3 can be loaded so as to be aligned in a longitudinal direction in the holder 51a. Hereinafter, the radiographic image capturing device(s) is/are referred to as radiographic image capturing device(s) P in a case where the explanation is made without distinguishing the radiographic image capturing devices P1 to P3 and a case of indicating a single radiographic image capturing device.

A radiation generator 52 is provided in the capturing room Ra, and as shown in FIG. 1, the radiation generator 52 which is used for long image capturing can perform long image capturing (that is, one-shot long image capturing) by once emitting radiation to the plurality of radiographic image capturing devices P1 to P3 loaded in the capturing stand 52A via a patient which is a subject H.

In the capturing room Ra, there is also provided a relay 54 for relaying communication between devices in the capturing room Ra and devices outside the capturing room Ra and the like.

The relay 54 is provided with an access point 53 so that the radiographic image capturing devices P1 to P3 can transmit and receive signal values D, various signals and the like in a wireless system. The relay 54 is connected with a controller (generator) 55 of the radiation generator 52 and a console C.

As shown in FIG. 1, in a front room (also referred to as an operation room or the like) Rb, an operation device 57 of the radiation generator 52 is provided, and the operation device 57 is provided with an exposure stich 56 for the operator such as a radiologist to operate to instruct the radiation generator 52 to start radiation emission and the like.

In the front room Rb, there are also provided a console C which is configured by a computer in which a CPU (Central Processing Unit), a ROM (Read Only Memory), a RAM (Random Access Memory), an input/output interface and the like not shown in the drawings are connected to a bus. The console C is provided with a display Ca configured by a CRT (Cathode Ray Tube), an LCD (Liquid Crystal Display) and the like, and the console C includes an input unit such as a mouse and a keyboard not shown in the drawings. A storage Cb configured by an HDD (Hard Disk Drive) or the like is connected to or built in the console C.

Figure 15A:
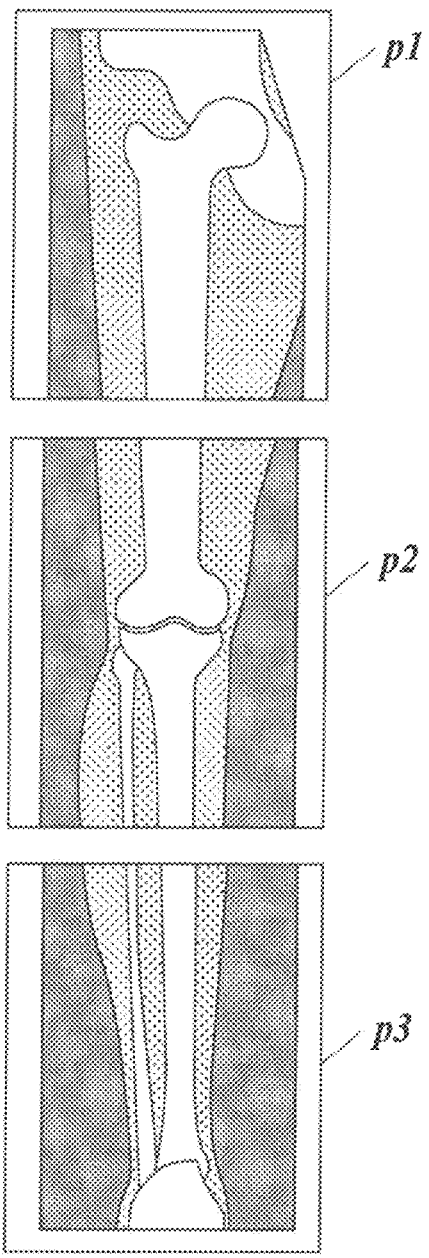
FIG. 15A This is a view showing an example of radiographic images captured by the long image capturing.
Figure 15B:
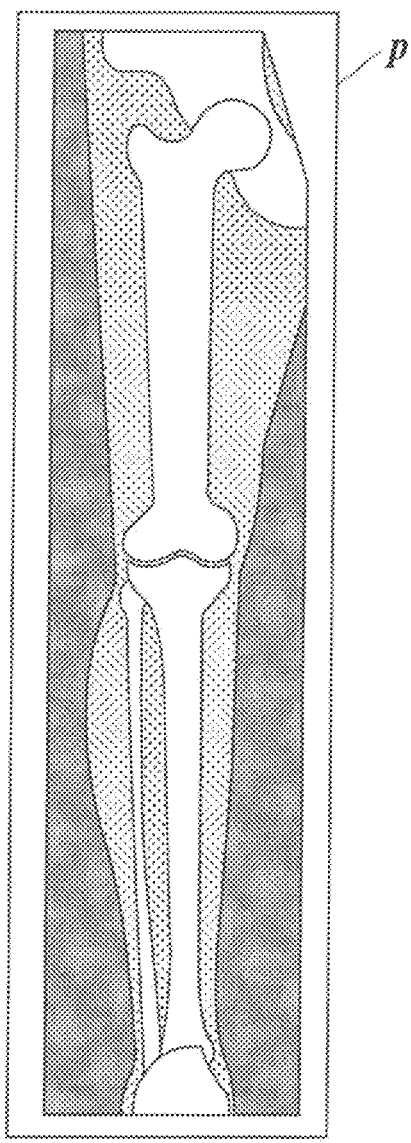
FIG. 15B This is a view showing an example of a combined image which is generated by combining the radiographic images.
Figure 16:
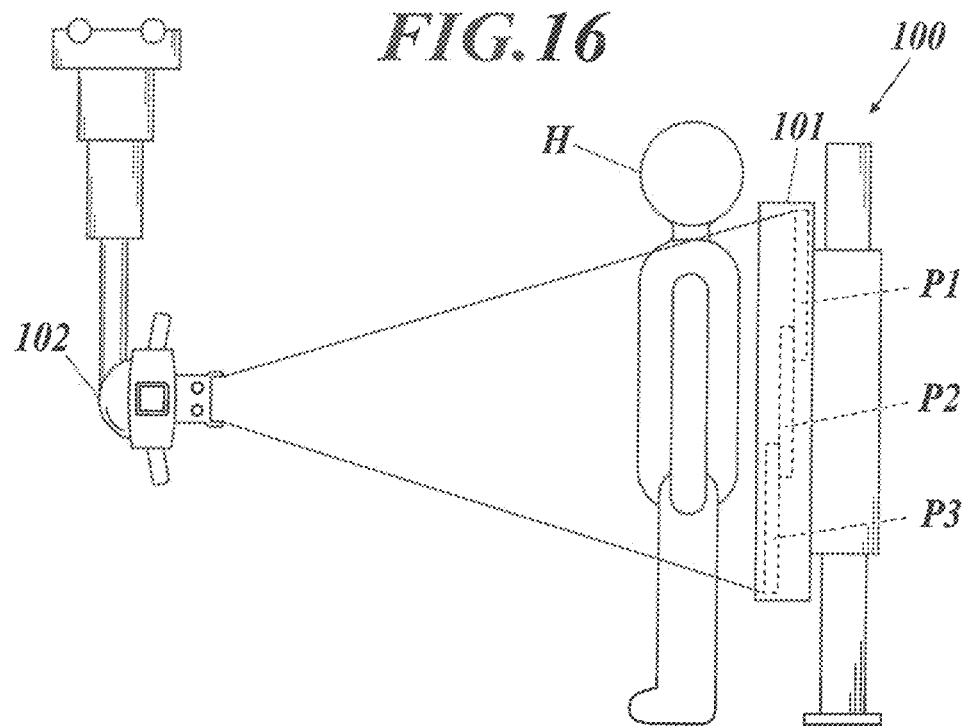
FIG. 16 This is a view explaining one-shot long image capturing.

In the embodiment, the console C generates radiographic images p1 to p3 (for example, see FIG. 15A) on the basis of the signal values D which were transferred from the radiographic image capturing devices P1 to P3, and combines the generated radiographic images p1 to p3 to generate a combined image p (for example, see FIG. 15B). This will be described in detail later.

[Radiographic Image Capturing Device]

Figure 2:
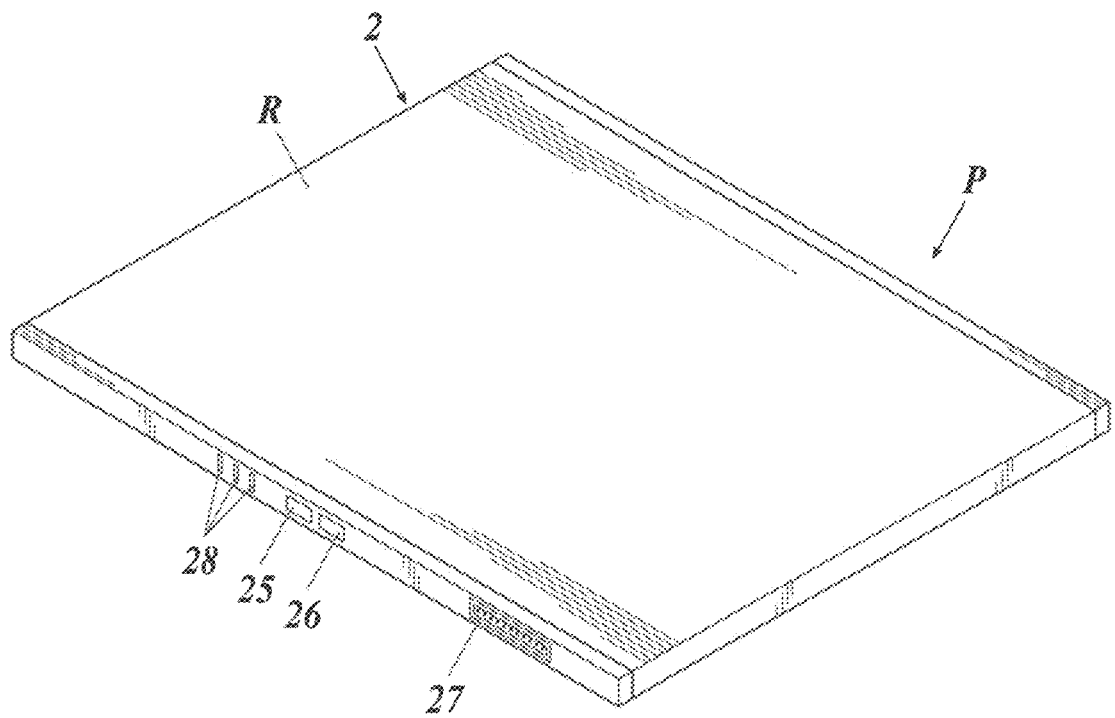
FIG. 2 This is a perspective view showing the outer appearance of a radiographic image capturing device.

Next, the radiographic image capturing device P used in the radiographic image capturing system will be described. FIG. 2 is a perspective view showing the outer appearance of the radiographic image capturing device. In the embodiment, the radiographic image capturing device P is configured by containing after-mentioned radiation detectors 7 and the like in a casing 2, and a power switch 25, a switching switch 26, the above-described connector 27, indicators 28 and the like on one lateral surface of the casing 2. Though not shown in the drawings, in the embodiment, an antenna 29 (see the following FIG. 3) for performing wireless communication with the outside is provided on the opposite lateral surface of the casing 2, for example.

Figure 3:
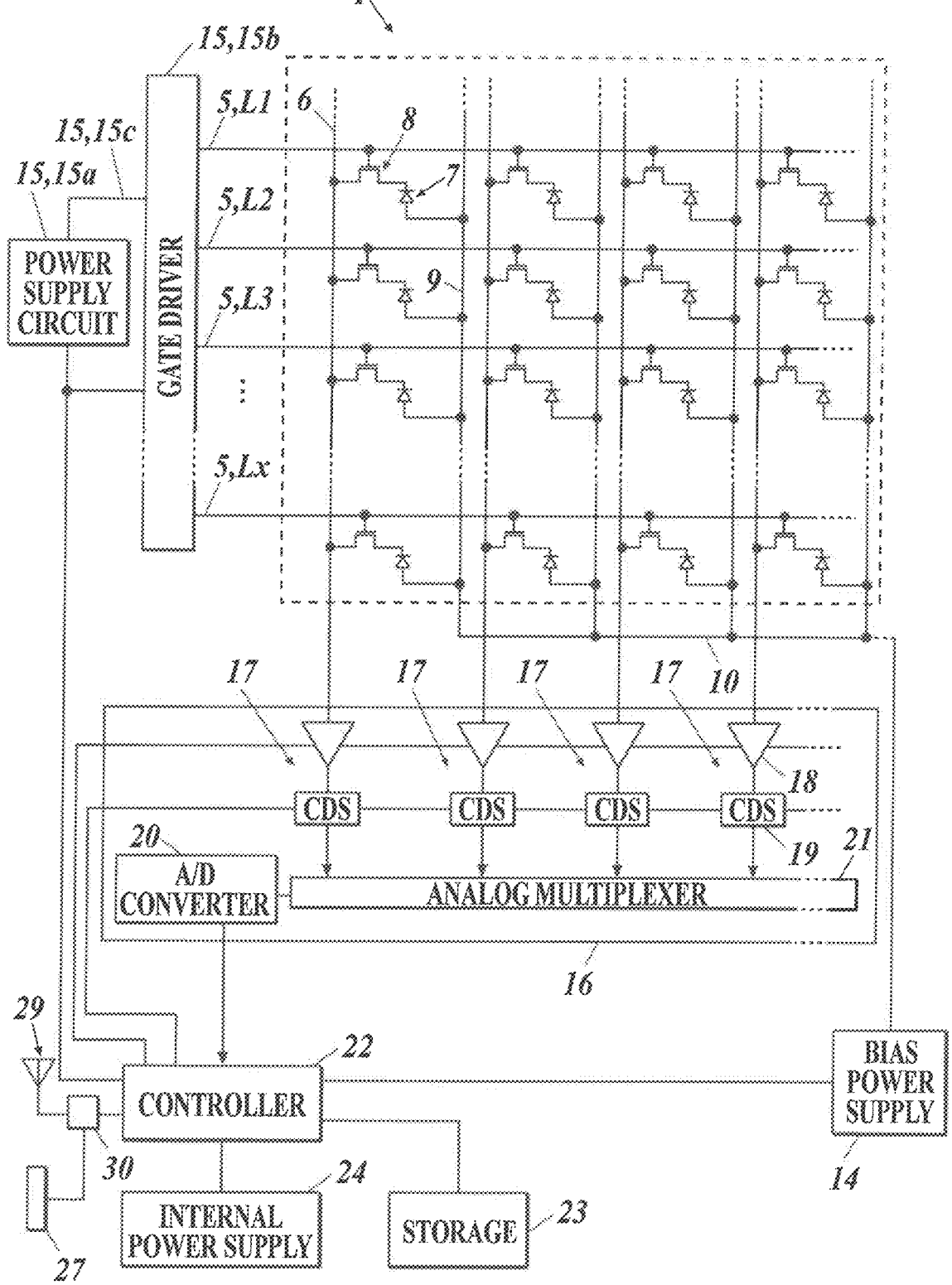
FIG. 3 This is a block diagram showing an equivalent circuit of the radiographic image capturing device.

FIG. 3 is a block diagram showing an equivalent circuit of the radiographic image capturing device. As shown in FIG. 3, in the radiographic image capturing device P, a plurality of radiation detectors 7 is arranged two-dimensionally (in matrix) on a sensor substrate not shown in the drawings. Each of the radiation detectors 7 generates an electrical charge corresponding to the dose of the emitted radiation.

The radiation detectors 7 are connected to respective bias lines 9, which are connected to respective connecting lines 10. The connecting lines 10 are connected to a bias power supply 14. The bias power supply 14 applies an inverse bias voltage to the radiation detectors 7 via the bias lines 9 and the like.

The radiation detectors 7 are connected to thin film transistors (hereinafter, referred to as TFTs) 8, which serve as switching elements and are connected to respective signal lines 6. A scan driver 15 switches ON and OFF voltages supplied from a power supply circuit 15a via a line 15c at a gate driver 15b, and applies the voltages to lines L1 to Lx of scanning lines 5.

The TFTs 8 are turned off in response to an OFF voltage applied via the scanning lines 5 to disconnect the radiation detectors 7 and the respective signal lines 6. At the time of capturing, radiation is emitted to the radiographic image capturing device P while the TFTs 8 are turned off by the application of OFF voltage to the TFTs 8 via the scanning lines 5 for a predetermined time, and the electrical charges generated in the radiation detectors 7 by the radiation irradiation are accumulated in the radiation detectors 7.

The TFTs 8 are turned on in response to an ON voltage applied via the scanning lines 5 and cause the electrical charges accumulated in the radiation detectors 7 to be released to the signal lines 6. A plurality of reading circuits 17 is provided in a reading IC 16 and connected to the respective signal lines 6.

During the reading processing of signal values D, electrical charges released from the radiation detectors 7 flow into the reading circuits 17 via the signal lines 6, and voltage values corresponding to the amount of electrical charges are output from amplifier circuits 18. Correlated double sampling circuits ("CDSs" in FIG. 3) 19 read the voltage values from the amplifier circuits 18 and output analog signal values D. The output signal values D are sequentially sent to an A/D converter 20 via an analog multiplexer 21, sequentially converted to digital signal values D at the A/D converter 20, and output to be sequentially stored in a storage 23.

A controller 22 is configured by including a computer (not shown) provided with a CPU, a ROM, a RAM, an input/output interface and the like connected to a bus, and a field programmable gate army (FPGA). The controller 22 may be composed of a dedicated controller circuit.

The controller 22 is connected to the storage 23 provided with a static RAM (SRAM), a synchronous DRAM (SDRAM), and a NAND flash memory, and a communicator 30 that establishes wired or wireless communication with the outside via the antenna 29 or the connector 27. The controller 22 is further connected to an internal power supply 24 such as a lithium ion capacitor.

In the embodiment, the controller 22 of the radiographic image capturing device P turns off the TFTs 8 for a predetermined time in a state in which radiation is not emitted to the radiographic image capturing device P before or after the capturing, thereafter reads the electrical charges accumulated in the radiation detectors 7 by the reading circuit 17 similarly to the above reading processing of the signal values D, and thereby obtains offset data O caused by dark charges (also referred to as dark current).

[Generation of Combined Image for Output in Image Generator]

Next, brief explanation is made for generation processing of radiographic images p1 to p3 based on signal values D and the like read by the plurality of radiographic image capturing devices P1 to P3 (see FIG. 1) and generation processing of a combined image p (that is, combined image p for output which is finally output to an external system from the image generator) combining the radiographic images p1 to p3 in the image generator of the radiographic image capturing system 50 (see FIG. 1) according to the embodiment.

Though the following explanation is made for a case of configuring the console C to function as the image generator and the console C is described as an image generator C, for example, the controller 22 of the radiographic image capturing device P (in a case where there are a plurality of radiographic image capturing devices P as shown in FIG. 1, the controller 22 of one of the radiographic image capturing devices P, for example) may perform the following processing (that is, the image generator 22 of the radiographic image capturing device P may function as the image generator). The image generator may be configured as a device other than the console C and the generator 22 of the radiographic image capturing device P.

Though the following explanation is made for a case of using a display Ca (see FIG. 1) of the above-mentioned console C as the display which displays the combined image p and the like, the display may be configured as a display device other than the display Ca of the console C.

As described above, when the long image capturing is performed, in the radiographic image capturing devices P1 to P3, the offset data O is subjected to subtraction processing for each of the radiation detectors 7 from the signal values D which were read according to the following formula (1), and the calculated real signal values D* (that is, signal values caused by electrical charges generated by radiation emission) are transferred to the image generator C. The subtraction processing of the following formula (1) may be performed by the image generator C.

$$D^* = D - O \qquad (1)$$

The image generator C performs image processing such as normalization processing, gain processing and gradation processing corresponding to the capturing site to the real signal values D* and generates the radiographic images p1 to p3 (for example, see FIG. 15A). Then, the image generator C performs noise removal, defective pixel correction and the like to the generated radiographic images p1 to p3, and performs processing of removing what is called grid patterns since the grid patterns appear in the radiographic images p1 to p3 in a case of capturing using a grid not shown in the drawings.

The image generator C generates the combined image p for output (for example, see FIG. 15B) by combining the radiographic images p1 to p3 after adjusting the density, position, enlargement factor and the like of the radiographic images p1 to p3 which were subjected to the image correction processing as described above.

At that time, in a case where long image capturing is performed by one-shot long image capturing (see FIG. 1), there are portions where the radiographic image capturing devices p overlap with each other in a front-back direction (that is, front-back direction when seen from the radiation generator 52) in the holder 51a of the capturing stand 51.

When radiation is emitted from the radiation generator 52, as shown in the enlarged sectional view of FIG. 4, the casing 2a of the radiographic image capturing device Pa on the front side (side closer to the radiation generator 52 (not shown in FIG. 4)) and structures inside the radiographic image capturing device Pa such as the sensor panel Spa (including the sensor substrate having the radiation detectors 7 (see FIG. 3) which are two-dimensionally arranged as described above) and the like appear in the radiographic image which is captured by the radiographic image capturing device Pb on the back side (that is, the side away from the radiation generator 52).

Figure 5A:
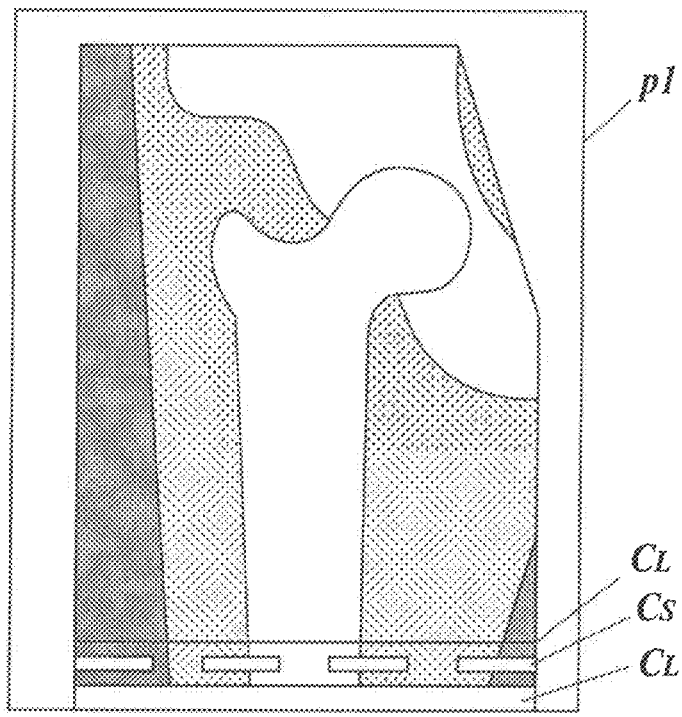
FIG. 5A This is a view showing streaky components $C_L$ and structural components $C_S$ in a radiographic image p1.
Figure 5B:
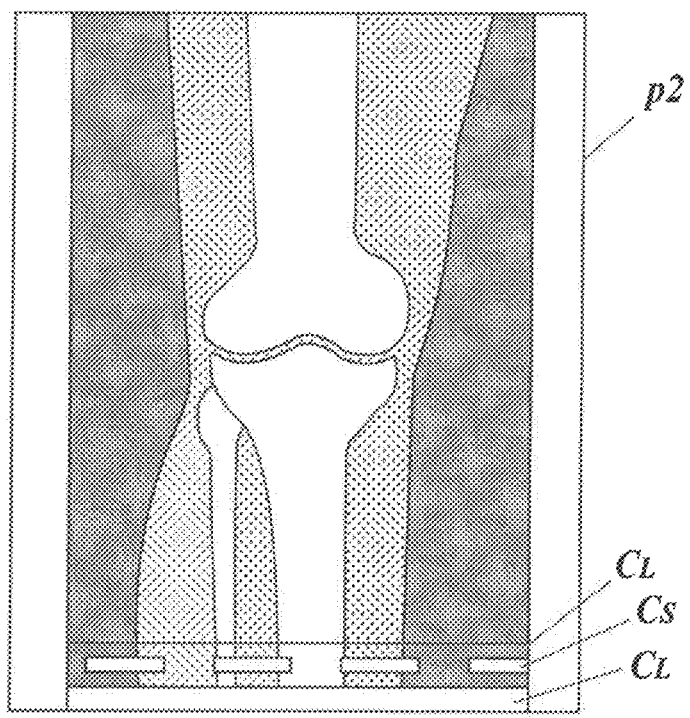
FIG. 5B This is a view showing streaky components $C_L$ and structural components $C_S$ in a radiographic image p2.

Thus, streaky components $C_L$ like a horizontal streak caused by a straight line structure such as edge portions of internal structures of the casings 2 of the radiographic image capturing devices P2 and P3 on the front side and the sensor panels SP and structural components $C_S$ caused by the structures inside the casings 2 of the front radiographic image capturing devices P2 and P3 appear as shown in FIGS. 5A and 5B on the radiographic image p1 captured by the radiographic image capturing device P1 arranged on the back side of the radiographic image capturing device P2 shown in FIG. 1 and the radiographic image p2 captured by the radiographic image capturing device P2 arranged on the back side of the radiographic image capturing device P3.

Thus, in a case where the long image capturing is performed by one-shot long image capturing, the image generator C performs processing such as removing of the streaky components $C_L$ and the structural components $C_S$ from radiographic images p1 and p2 among the radiographic images p1 to p3 which were generated and subjected to the image correction and the like as mentioned above and combines the radiographic images p1 to p3 to generate the combined image p for output. The removing of the streaky components $C_L$ and the structural components $C_S$ and the like are described in Japanese Patent Application No. 2015-082439, which is to be referred to for details.

[Generation, Displaying and Others of Combined Image for Check in Image Generator]

Next, generation processing, display processing and the like of a combined image for check and a method for generating and displaying the combined image for check in the image generator C of the radiographic image capturing system 50 (see FIG. 1) according to the embodiment will be described. The description will be also made together for the actions of the radiographic image capturing system 50 and the method for generating and displaying the combined image for check according to the embodiment.

In the embodiment, before the image generator C generates the above-mentioned combined image p for output, the image generator C generates a combined image ppre for check and displays the image ppre for check on the display Ca (see FIG. 1) for the operator such as a radiologist to look at the image ppre for check and determine whether the retake is necessary and the like.

However, if the combined image ppre for check is generated in a manner similar to that of the combined image p for output, a very long time of approximately tens of seconds is required from emission of radiation for long image capturing to generation of the combined image ppre for check and display of the image ppre for check on the display Ca as mentioned above, thus leading to late start of the checking work by the operator.

Thus, in the embodiment, before generation of the combined image p for output as described above, the image generator C replaces processing from among generation of the radiographic images p1 to p3, image processing to the radiographic images p1 to p3 and generation of the combined image p for output with simplified processing to generate the combined image ppre for check and displays the combined image ppre for check on the display Ca.

In the embodiment, the image generator C generates the combined image p for output in a case where the combined image ppre for check displayed on the display Ca is approved by the operator such as a radiologist. The image generator C can be configured to generate the combined image p for output regardless of approval by the operator. The description will be made later for a case where the combined image ppre for check is not approved by the operator.

The above processing includes, for example, above-mentioned noise removal processing, defective pixel correction processing, processing of removing the grid patterns, processing such as positioning of the radiographic images p1 to p3 when combining the images p1 to p3, and processing of removing the streaky components $C_L$ and the structural components $C_S$ from the radiographic images p1 and p2. The simplified processing indicates processing which is completed in a time shorter than the time required for the original processing while obtaining results similar to the original processing.

That is, for example, in a case of removing the grid patterns from the radiographic image p, image analysis of the radiographic image p is performed by using Fourier transform, for example, the grid pattern components are extracted and the components are removed from the radiographic image p in the original processing, whereas, in the simplified processing, image analysis or the like of the radiographic image p is not performed and the processing is performed to remove grid pattern components which are created in advance from the radiographic image p, for example.

When any of the processing in each process for generating the combined image p for output is replaced with simplified processing, a single piece of processing may be replaced with simplified processing, or a plurality of pieces of processing may be replaced with respective pieces of simplified processing.

[Effect]

As described above, according to the radiographic image capturing system 50 and the method for generating and displaying the combined image for check according to the embodiment, the image generator C generates the combined image ppre for check and displays the image on the display Ca before generating the combined image p for output. When the combined image ppre for check is generated, since the combined image ppre for check is generated by replacing the original processing with simplified processing as described above, it is possible to greatly shorten the time to be approximately several seconds, the time being a time required from emission of radiation for the long image capturing to generation of the combined image ppre for check and displaying of the image on the display Ca.

Thus, the operator such as a radiologist can look at the combined image ppre for check which was promptly (that is, earlier than conventional cases) displayed after emission of radiation, to determine whether retake is necessary or the like, and the operator can promptly proceed to next capturing or next processing. As for the patient which is the capturing target of the long image capturing, since the time until the patient is released by the determination of the operator that the retake is not necessary is shortened, the binding time of the patient is shortened, and it is possible to reduce the load on the patient.

[Specific Examples of Radiographic Image Capturing System and Method for Generating and Displaying Combined Image for Check]

The above simplified processing includes, for example, processing of using what is called thinned data Dpre which was extracted from the read signal values D instead of using all the signal values P read in the radiographic image capturing devices P1 to P3 (see FIG. 1) as data which is the basis for generation of the combined image ppre for check as described above.

Hereinafter, though specific description will be made for a case of generating and displaying the combined image ppre for check by extracting the thinned data Dpre instead of the signal values D in such a way, the present invention is not limited to this, and the present invention may include any embodiment which replaces processing among the processing in each process for generating the combined image p for output with simplified processing to generate and display the combined image ppre for check as described above.

[Extraction of Thinned Data and Others]

In the embodiment, the controller 22 of the radiographic image capturing device P performs the extraction processing of the thinned data Dpre from the signal values D, and when radiation is emitted to the radiographic image capturing device P and long image capturing is performed, the controller 22 reads out the signal values D from the respective radiation detectors 7 as described above. The thinned data Dpre is extracted at a predetermined rate from the read signal values D, and the extracted thinned data Dpre is transferred to the image generator C.

The extraction processing of this thinned data Dpre may be performed by the image generator C. In this case, when the signal values D are read out as described above, the controller 22 of the radiographic image capturing device P transfers the signal values D to the image generator C, and the image generator C extracts the thinned data Dpre at a predetermined rate from among the transferred signal values D.

As for the method for extracting the thinned data Dpre, for example, as shown in FIG. 6, the thinned data Dpre may be formed by extracting the signal values D (n, m) read from the radiation detectors 7 connected to the scanning lines 5 which were specified at a rate of one for every predetermined number (four in FIG. 6) of scanning lines 5 as shown by shaded area in the drawing from the read signal values D (n, m).

In FIG. 6, L1, L2 . . . indicate the lines L1, L2 . . . (see FIG. 3) of the scanning lines 5, and D (n, m) indicates the signal value D read out from the radiation detector 7 (n, m) of the n-th line and m-th row among the two-dimensionally arranged radiation detectors 7. The method for extracting the thinned data Dpre is not limited to this, and for example, the thinned data Dpre may be extracted by extracting the signal values D at a rate of one from the signal values D read out from 3×3 or 4×4 radiation detectors 7, for example.

In the embodiment, as mentioned above, the controller 22 of the radiographic image capturing device P obtains offset data O before or after the long image capturing. As described above, when the thinned data Dpre is extracted from among the signal values D, the subtraction processing is performed for each of the radiation detectors by subtracting the offset data O from the thinned data Dpre in accordance with the following formula (2) similar to the above formula (1), thinned data Dpre_cor (hereinafter referred to as thinned correction data Dpre_cor) which was subjected to the offset correction is obtained, and the calculated thinned correction data Dpre_cor is transferred to the image generator C.

$$Dpre\_cor = Dpre\_raw - O \quad (2)$$

In the above formula (2), Dpre_raw indicates raw data before offset correction (that is, the thinned data Dpre extracted from the signal values D). Hereinafter, the data is referred to as thinned raw data Dpre_raw in order to be distinguished from the thinned correction data Dpre_cor. The thinned raw data and the offset data O may be transferred to the image generator C from the radiographic image capturing device P to perform the subtraction processing of the above formula (2) in the image generator C.

In the embodiment, when radiation is emitted to perform the long image capturing, the radiographic image capturing devices P1 to P3 (see FIG. 1) perform the reading processing of the signal values D and the above extraction processing, and transfer the thinned raw data Dpre_raw to the image generator C. In a case of performing the acquisition processing of the offset data O after the capturing, the thinned correction data Dpre_cor is transferred to the image generator C after the acquisition processing of the offset data O is performed.

That is, in the embodiment, the radiographic image capturing devices P1 to P3 transfer the two types of thinned data Dpre (thinned raw data Dpre_raw and thinned correction data Dpre_cor) which are processed differently to the image generator C.

When the thinned correction data Dpre_cor is transferred to the image generator C, the radiographic image capturing devices P1 to P3 perform the subtraction processing for each of the radiation detectors 7 by subtracting the offset data O from the remaining signal values D (that is, signal values D other than the thinned raw data Dpre_raw) in accordance with the formula (1), and transfers the real signal values D* regarding the remaining signal values D which were calculated to the image generator C. The above subtraction processing may be performed by the image generator C by transferring the remaining signal values D and the corresponding offset data O to the image generator C from the radiographic image capturing devices P1 to P3.

[Displaying Example on Display]

Next, description will be made for how to generate the combined image ppre for check and the like and display the image on the display Ca in the image generator C (see FIG. 1) by showing a displaying example on the display Ca.

Figure 7:
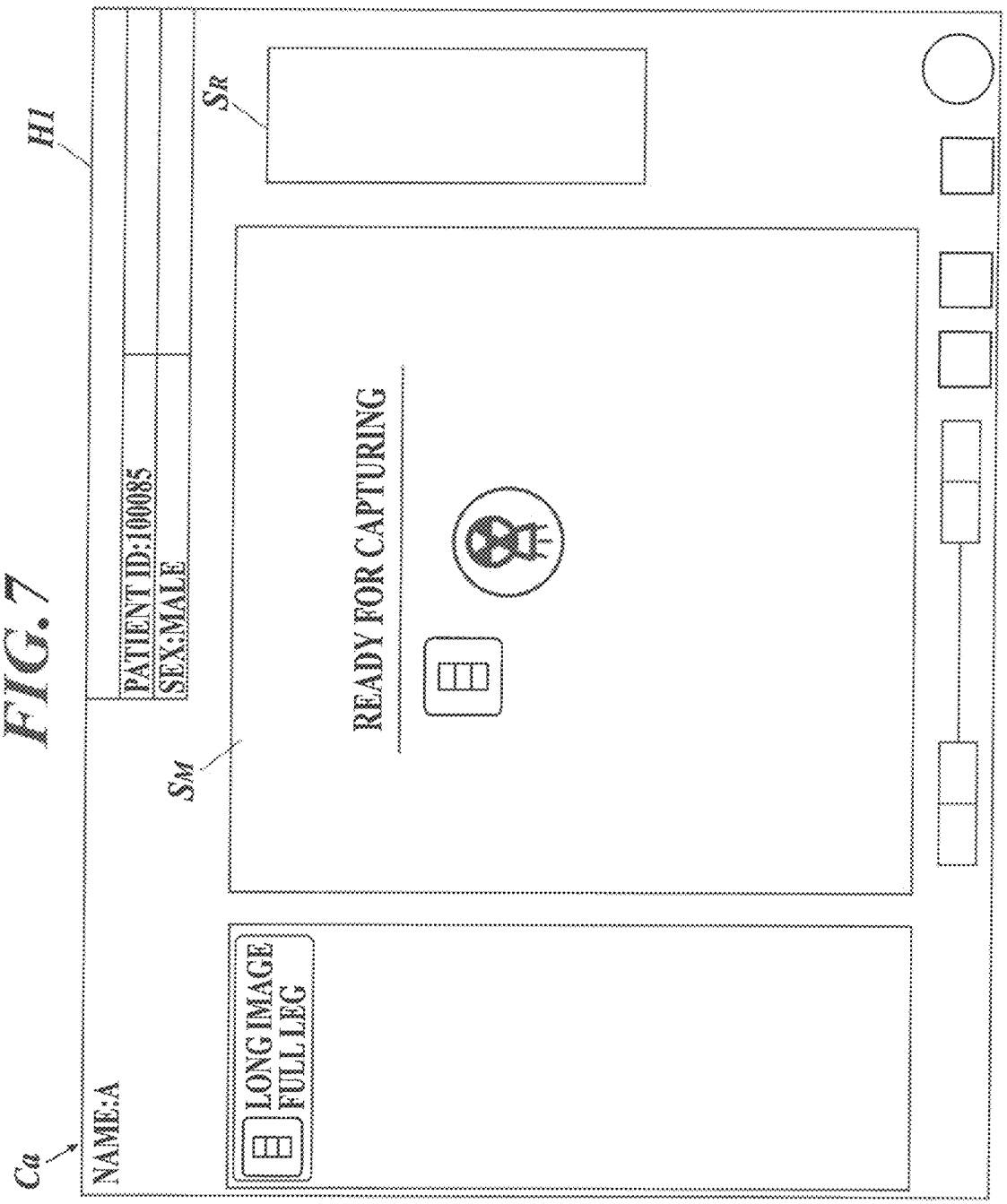
FIG. 7 This is a view showing an example of a display screen displayed on a display.

In the embodiment, when the long image capturing is performed, a display screen H1 as shown in FIG. 7 is displayed on the display Ca, for example. Specifically, the display screen H1 is provided with a main screen $S_M$ at a nearly center and a sub-screen $S_R$ on the right side. For example, when the radiographic image capturing devices P1 to P3 are loaded into the holder 51a of the capturing stand 51 and becomes ready for capturing, as shown in FIG. 7, "ready for capturing" or the like is displayed on the main screen $S_M$, for example, to notify the operator such as a radiologist that the radiographic image capturing devices P1 to P3 are ready for the capturing.

When radiation is emitted from the radiation generator 52 to the radiographic image capturing devices P1 to P3 to perform long image capturing and the thinned raw data Dpre_raw is transferred from the radiographic image capturing devices P1 to P3 as described above, the image generator C generates the radiographic images ppre_raw1 to ppre_raw3 (not shown in the drawings) by performing each processing including the simplified processing as described above to the transferred thinned raw data Dpre_raw, and generates the combined image ppre for check (hereinafter, referred to as the combined image ppre_raw for check) by combining them.

Figure 8:
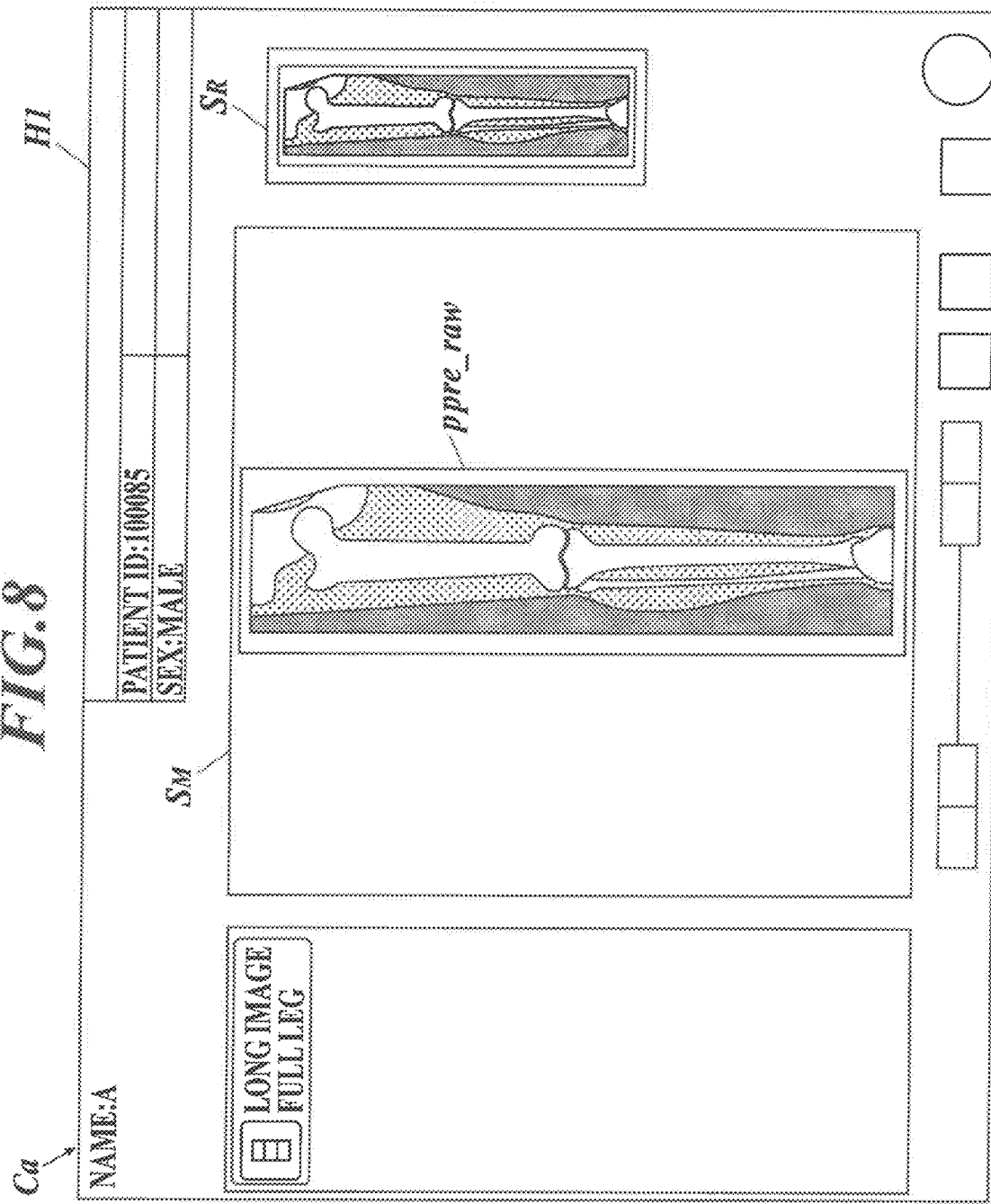
FIG. 8 This is a view showing a state in which combined image ppre_raw for check is displayed on the display.

As shown in FIG. 8, the image generator C causes the main screen $S_M$ of the display screen H1 displayed on the display Ca to display the generated combined image ppre_raw for check. The image generator C also causes the sub-screen $S_R$ to display a thumbnail image of the combined image ppre_raw for check. In this case, as mentioned above, since the thinned raw data Dpre_raw is data which is not subjected to the offset correction using the offset data O, the combined image ppre_raw for check which was generated on the basis of the thinned raw data Dpre_raw is an image of a relatively low quality.

However, by looking at the combined image ppre_raw for check displayed on the display screen H1, the operator such as a radiologist can determine whether the capturing site of the patient is captured in the image (that is, whether nothing is captured in the combined image), whether the emission field of radiation is appropriately set, whether the capturing site is broken (whether the capturing site is located out of the image) and the like.

Next, when the thinned correction data Dpre_cor is transferred from the radiographic image capturing devices P1 to P3 as described above, the image generator C generates the radiographic images ppre_cor1 to ppre_cor3 (not shown in the drawings) by performing each processing including the processing which was simplified similarly to the above with respect to the transferred thinned correction data Dpre_cor, and generates the combined image ppre for check (hereinafter, referred to as the combined image ppre_cor for check) by combining them.

Figure 9:
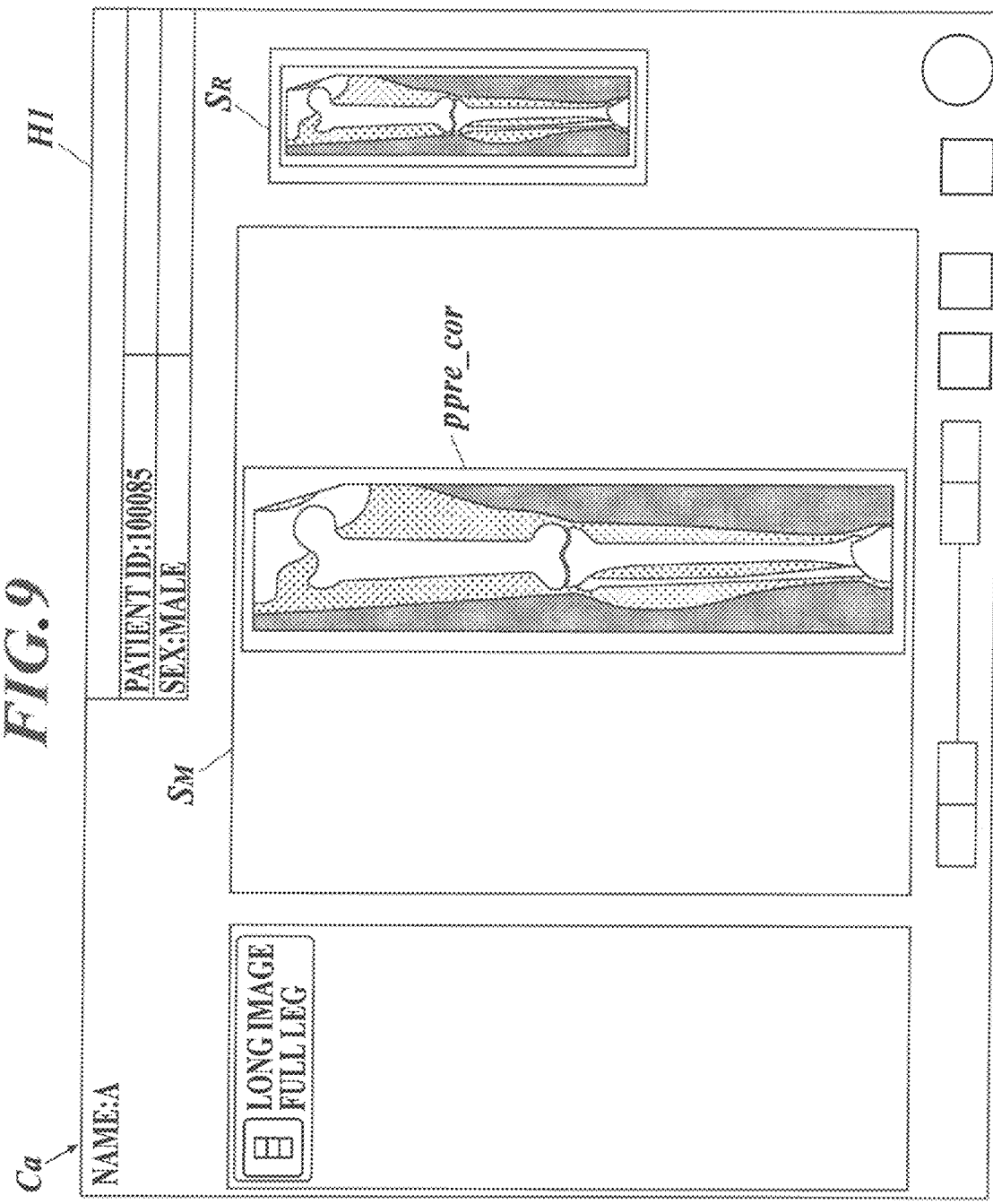
FIG. 9 This is a view showing a state in which combined image ppre_cor for check is displayed on the display.

As shown in FIG. 9, the image generator C causes the main screen $S_M$ to display the generated combined image ppre_cor for check in such a manner of replacing the combined image ppre_raw for check (see FIG. 8) displayed on the main screen $S_M$ of the display screen H1 with the combined image ppre_cor for check.

In this way, in the embodiment, the image generator C generates a plurality of combined images ppre_raw and ppre_cor for check which are processed differently, and causes the display Ca to display the plurality of combined images ppre_raw and ppre_cor for check in the generated order in such a manner that the combined image ppre_raw for check which was generated earlier is replaced with the combined image ppre_cor for check which was generated later.

By such a configuration, compared with a case of displaying only a single type of combined image ppre_cor for check, the combined image ppre_raw for check can be displayed on the display Ca more promptly (earlier) after emission of radiation, the operator such as a radiologist can look at the combined image ppre_raw for check more promptly (earlier) to determine whether retake is necessary and the like, and the processing can proceed to the next capturing or next processing more promptly. As for the patient which is the capturing target of long image capturing, since the time until the patient is released by the determination of the operator that the retake is not necessary is shortened more, binding time of the patient is shortened more, and thus enabling further reduction of load on the patient.

When the real signal values D* regarding the remaining signal values D are transferred from the radiographic image capturing devices P1 to P3 as described above, the image generator C executes the above-mentioned real processing to the real signal values D* to generate the radiographic images p1 to p3 (see FIG. 15A), and combines them to generate the combined image p for output (see FIG. 15B).

Figure 10:
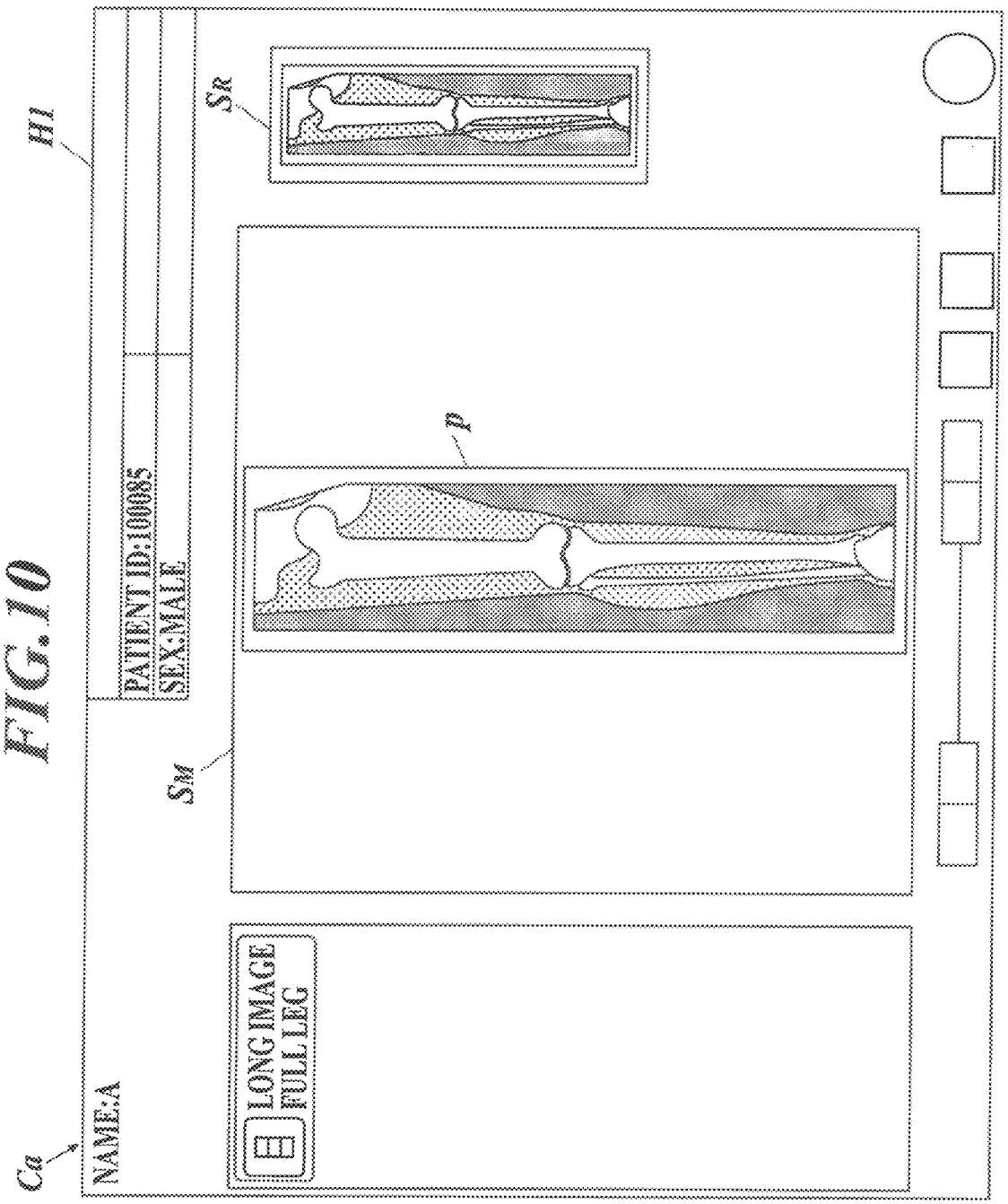
FIG. 10 This is a view showing a state in which a combined image for output is displayed on the display.

In the embodiment, as shown in FIG. 10, the image generator C causes the generated combined image p for output to be displayed in such a manner of replacing, with the combined image p for output, the combined image ppre_cor for check (see FIG. 9) which was displayed on the main screen $S_M$ of the display screen H1. The combined image p for output does not necessarily need to be displayed on the display Ca.

In the embodiment, when the combined image ppre_raw for check is generated, the image generator C does not cause the midway images (that is, radiographic images ppre_raw1 to ppre_raw3, for example) to be displayed on the display screen H1 displayed on the display Ca, and as shown in FIG. 8, at the time when the combined image ppre_raw for check is generated, the image generator C causes the combined image ppre_raw for check to be displayed on the display Ca.

In this case, in a case of one-shot long image capturing as in the embodiment, when the reading processing of the signal values D are performed in the radiographic image capturing devices P1 to P3 by emitting radiation to the respective radiographic image capturing devices P1 to P3 from the radiation generator 52, the thinned raw data Dpre_raw is assumed to be transferred all at once to the image generator C from the radiographic image capturing devices P1 to P3.

Figure 14:
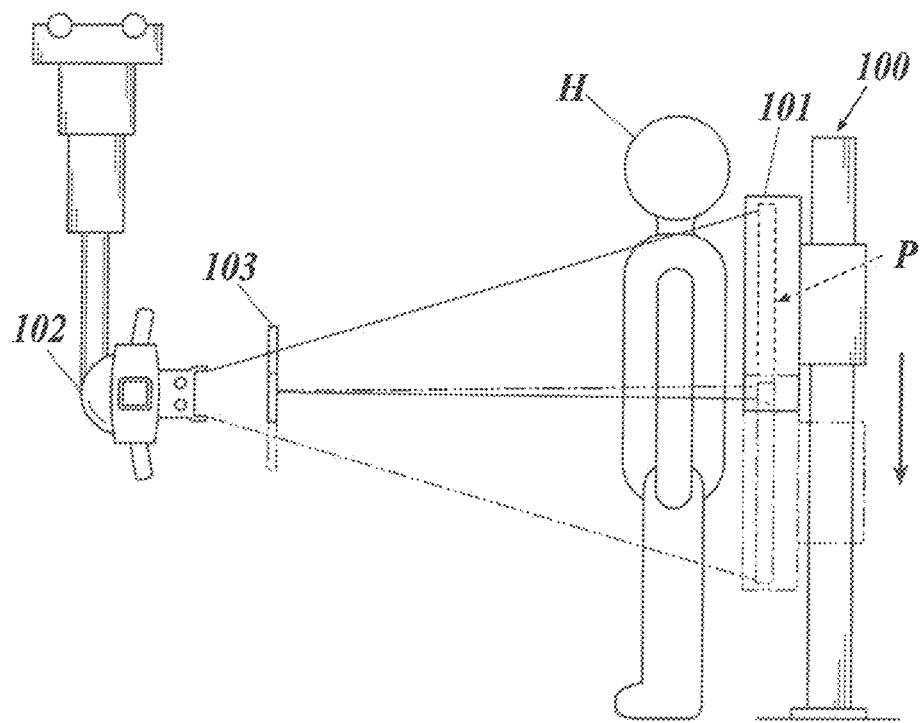
FIG. 14 This is a view explaining conventional moving type long image capturing.

However, even in a case of the one-shot long image capturing as in the embodiment, if the communication environment for wireless communication is bad, the thinned raw data Dpre_raw is transferred sequentially (that is, for each radiographic image capturing device P) from the radiographic image capturing devices P1 to P3 in some cases. Even in a case of moving type long image capturing as shown in FIG. 14, the signal values D are read each time radiation is emitted from the radiation generator 52 while moving the radiographic image capturing device P, leading to a state in which the thinned raw data Dpre_raw is transferred sequentially.

In such a case where the thinned raw data Dpre_raw is sequentially transferred from the radiographic image capturing devices P1 to P3 (or the radiographic image capturing device P in a case of FIG. 14), the image generator C may cause the display Ca to display nothing until the combined image ppre_raw for check is generated similarly to the above case.

However, in such a case, the image generator C may cause the generated radiographic images ppre_raw1 to ppre_raw3 to be displayed on the display Ca until there are obtained all the radiographic images ppre_raw1 to ppre_raw3 necessary for generating the combined image ppre_raw for check.

Figure 11:
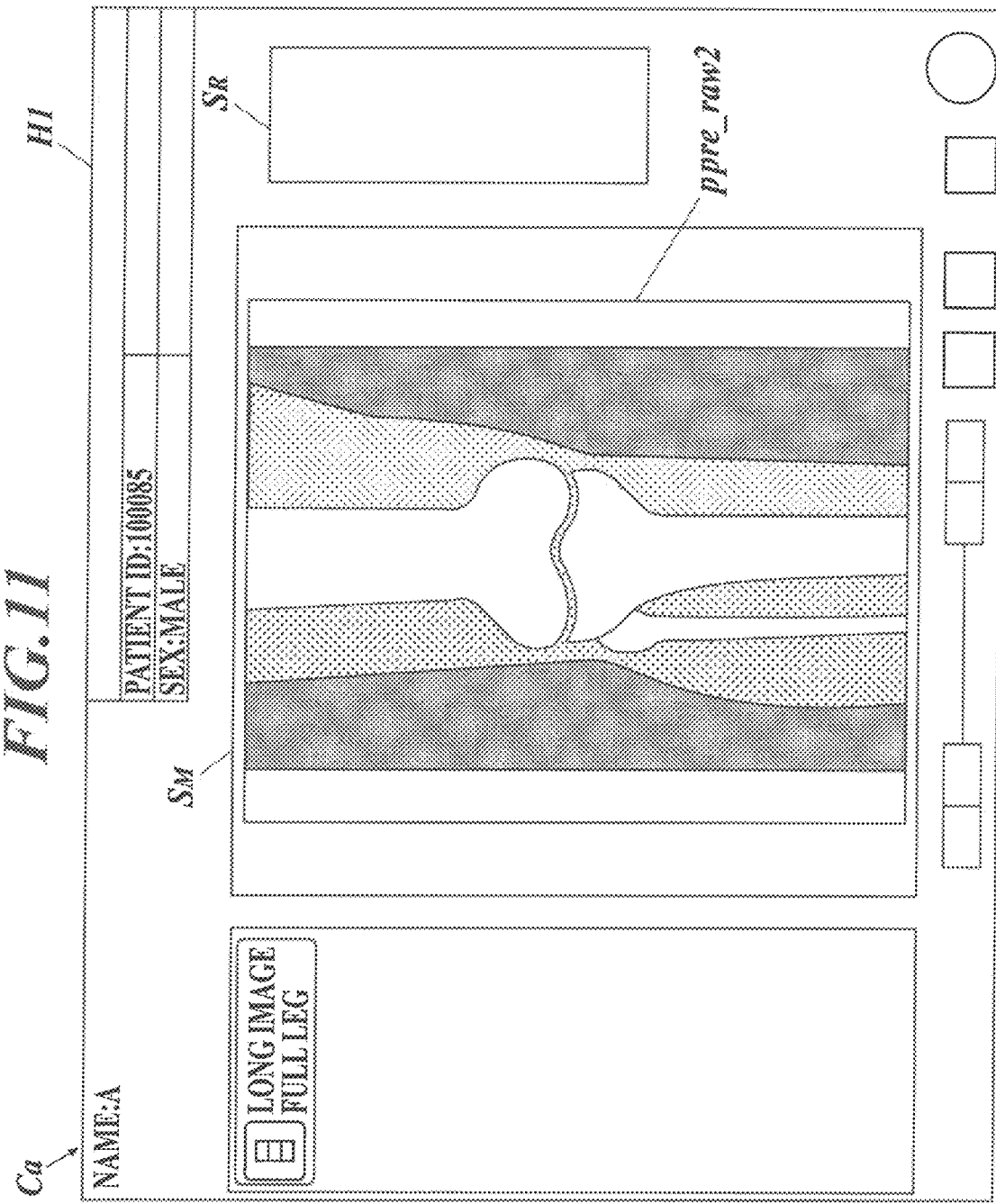
FIG. 11 This is a view showing a state in which the generated radiographic image is displayed on the display.

In this case, as shown in FIG. 11, for example, each time the generated radiographic images ppre_raw1 to ppre_raw3 are generated, it is possible to sequentially display the generated radiographic images ppre_raw1 to ppre_raw3 (FIG. 11 shows a case of the radiographic image ppre_raw2) on the main screen $S_M$ of the display screen H1 on the display Ca.

Figure 12:
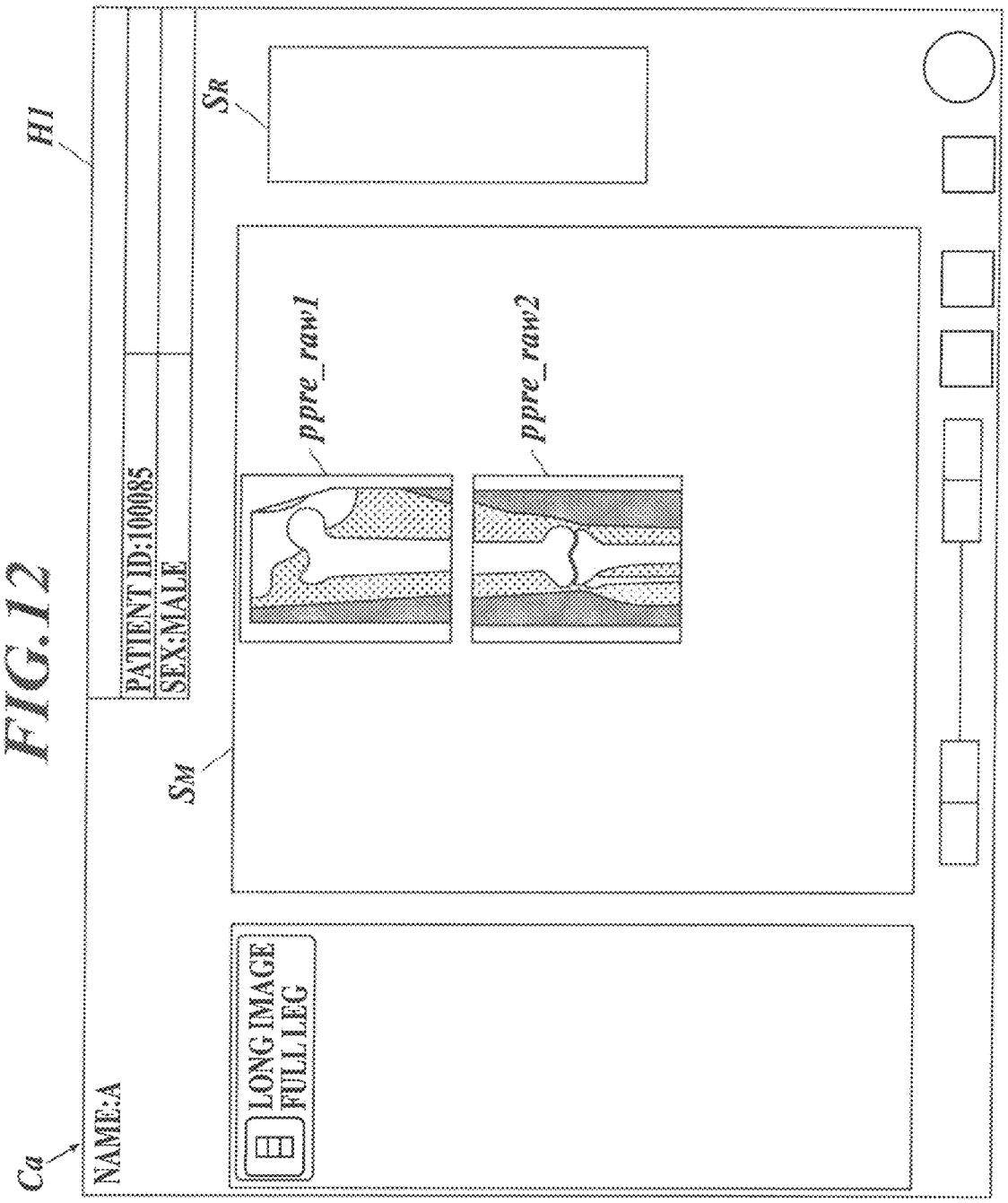
FIG. 12 This is a view showing a state in which generated radiographic images are displayed so as to be aligned on the display.

As shown in FIG. 12, for example, each time the generated radiographic images ppre_raw1 to ppre_raw3 are generated, it is also possible to display the generated radiographic images ppre_raw1 to ppre_raw3 to be aligned on the main screen $S_M$ of the display screen H1 on the display Ca (FIG. 12 shows a case where the image generation has been performed for up to the radiographic image ppre_raw2).

Figure 13:
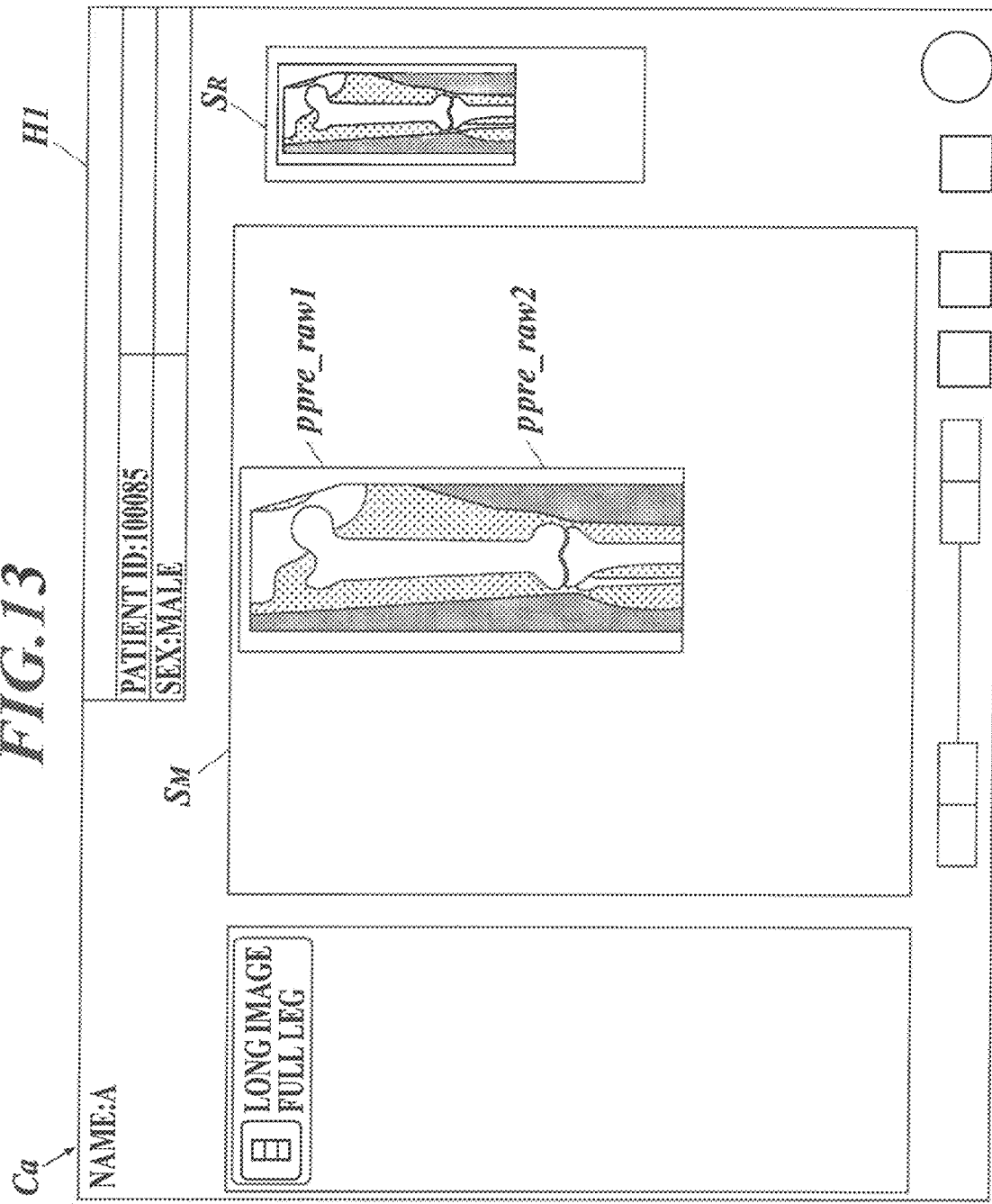
FIG. 13 This is a view showing a state in which the generated radiographic images are combined and displayed on the display.

Furthermore, when a radiographic image necessary for generating the combined image ppre_raw for check is generated, in a case where there is generated a radiographic image which can be combined with the radiographic image, the image generator C may combine the radiographic images and cause them to be displayed on the display Ca. That is, in this case, when the radiographic image ppre_raw2 is generated, for example, if the radiographic image ppre_raw1 which can be combined with the radiographic image ppre_raw2 is generated, as shown in FIG. 13, the image generator C may combine the radiographic images ppre_raw1 and ppre_raw2 and display the combined radiographic images ppre_raw1 and ppre_raw2 on the main screen $S_M$ of the display screen H1 on the display Ca.

The configuration as described above enables the operator such as a radiologist to determine whether retake is necessary by looking at the generated radiographic images ppre_raw1 to ppre_raw3 (in a case of FIGS. 11 and 12) and the combined radiographic images (in a case of FIG. 13) at the stage when the radiographic images ppre_raw1 to ppre_raw3 are generated without waiting for generation of the combined image ppre_raw for check, and thus, it is possible to determine whether retake is necessary more promptly (earlier) from emission of radiation.

[Image Editing and Others of Combined Image for Check]

In the image generator C according to the embodiment, the operator such as a radiologist can perform image editing to the combined image ppre_cor (see FIG. 9) for check displayed on the display Ca as described above. Though image editing to the combined image p (see FIG. 10) for output which was finally generated is a known matter, in the embodiment, it is possible to perform image editing for the combined image ppre_cor for check which is at the stage earlier than the stage of the combined image p for output.

The contents of the image editing are as follows, for example.

(A) Space Conversion enlargement/reduction (enlargement, reduction, fitting displaying (fitting in the width direction, height direction or the like), pixel same magnification and the like), panning, rotation, inversion and the like (B) Image Quality Adjustment density/contrast, frequency enhancement, sharpness enhancement, noise reduction, white/black inversion and the like (C) Combination Condition combination position, angle, overlapping (front and back), enlargement factor correction, reference density adjustment, combination correction condition (base correction) and the like (D) Overlay masking, marker, annotation, scale and the like (E) Image Cutting Out (cutting out an image at a free position from the combined image, as a new capturing image)

cutting position, cutting size and the like (F) Divided Output number of divided output, size of individual divided output image, position of individual divided output image, positioning by recognition of anatomical structure, use of information on test performed in the past and the like (G) Output Area trimming size, trimming position and the like Though the image editing has been conventionally started after generation of the combined image p for output, the above configuration enables to start image editing to the combined image earlier than a case of starting the image editing after generation of the combined image p for output since it is possible to start the image editing to the combined image ppre_cor for check at the state earlier than the stage of combined image p for output.

In the embodiment, the image generator C stores the contents of image editing which was actually performed to the combined image ppe_cor for check in such a way, and when the combined image p for output is generated as described above, the image generator C applies the image editing performed to the combined image ppre_cor for check to the combined image p for output which was generated, and performs the image editing automatically to the combined image p for output. The image editing which was automatically performed to the combined image p for output by the image generator C can also be slightly adjusted or changed by the operator such as a radiologist.

By such a configuration, the operator such as a radiologist does not need to perform image editing to the combined image p for output again if image editing is performed to the combined image ppre_cor for check, and even if the operator needs to slightly adjust or change the image editing which was automatically performed to the combined image p for output by the image generator C, the processing is finished in a short time, thus enabling generation of the combined image p for output earlier (more promptly).

Though the above embodiment (see FIG. 10) has been described for a case of replacing the combined image ppre_cor (see FIG. 9) for check displayed on the main screen $S_M$ of the display screen H1 with the combined image p for output when the image generator C generates the combined image p for output, the image editing is interfered if the combined image ppre_cor for check is replaced with the combined image p for output when the operator such as a radiologist is performing image editing to the combined image ppre_cor for check as described above.

Thus, the image generator C may not replace the image while the operator such as a radiologist is performing any image editing to the combined image ppre_cor for check even when the combined image p for output is generated, and may replace the combined image ppre_cor for check with the combined image p for output at the time when the image editing is determined to be settled or when the operator performed an operation indicating that the image editing was finished.

When the combined image ppre_cor for check is replaced with the combined image p for output, as described above, the image editing performed to the combined image ppre_cor for check may be applied to the combined image p for output to display the combined image p for output.

[Processing when Combined Image for Check is not Approved (Case of Failed Image)]

The description so far has been described for a case where the combined image ppre for check (that is, ppre_raw and ppre_cor, the same applies hereinafter) displayed on the display Ca by the image generator C was approved by the operator such as a radiologist (that is, a case where the combined image p for output is generated). However, in a case where the operator looking at the displayed combined image ppre for check determines that the retake is necessary, failed image processing is performed by clicking a predetermined button icon on the display screen H1 or the like.

In a case where failed image processing is performed, if the image generator C performs the combining processing despite that the combining processing is not necessary since the combined image p for output (see FIGS. 15B and 10) generated by combining the generated radiographic images p1 to p3 (see FIG. 15A) is not used, the image generator C delays start of the processing for retake and the other processing, finally leading to an unnecessarily long time for capturing.

Thus, in a case where the combined image ppre for check is not approved by the operator such as a radiologist who looked at the combined image ppre for check displayed on the display Ca and the failed image processing is performed, the image generator C may not perform the processing of combining the generated plurality of radiographic images p1 to p3, and may not perform the processing of generating the combined image p for output.

By such a configuration, in a case where the failed image processing is performed, the image generator C can start the processing for retake and the other processing promptly without performing combining processing of the generated radiographic images p1 to p3, which enables accurate shortening of the capturing time.

However, there can be a case where, though retake was performed, the combined image ppre for check obtained by capturing before performing the retake is better than the combined image ppre for check obtained by the retake (or combined image p for output). In such a case, the operator such as a radiologist performs cancelling operation of the failed image processing which was performed before by clicking a predetermined button icon on the display screen H1 or the like.

In such a case, at the time when the failed image processing was performed during capturing before retake, if the image generator C discards the generated plurality of radiographic images p1 to p3, retake needs to be performed again after the retake of a bad result, leading to not only a long capturing time but also increase in load on the patient and increase in the exposure dose of the patient. Thus, in a case of performing the failed image processing, it is preferable that the image generator C stores the generated radiographic images p1 to p3 in a memory though the combining processing of the radiographic images p1 to p3 is not performed as descried above.

In a case where the failed image processing was cancelled as described above, the image generator C may read out, from the memory, the plurality of radiographic images p1 to p3 which were generated and stored at the time of capturing before the retake, and restart the processing of combining the plurality of radiographic images p1 to p3 to generate the combined image p for output.

By such a configuration, in a case where the combined image ppre for check obtained by capturing before retake is better than the combined image ppre for check (or combined image p for output) obtained by the retake and the cancelling operation of the failed image is performed, it is possible to combine the plurality of radiographic images p1 to p3 which was generated at the time of capturing before the retake to generate the combined image p for output. Thus, retake is not necessary after the retake of the bad result, and it is possible to accurately prevent the capturing time from becoming longer and accurately prevent the increase in the load on the patient and the exposure dose of the patient.

[Modification Example]

The above embodiment has been described by assuming that the thinned data Dpre is transferred from the plurality of radiographic image capturing devices P1 to P3 (see FIG. 1) in one-shot long image capturing at the time of transferring the thinned data Dpre (Dpre_raw, Dpre_cor) to the image generator C from the radiographic image capturing devices P. The description also assumed that the thinned data Dpre is transferred from the radiographic image capturing device P as for the signal values D for each emission obtained by emitting radiation a plurality of times while moving the radiographic image capturing device P (see FIG. 14) by the moving type long image capturing.

However, in a case of one-shot long image capturing, for example, the thinned data Dpre may be transferred to the image generator C from any radiographic image capturing device P among the plurality of radiographic image capturing devices P1 to P3, and real signal values D* regarding the signal values D, not the thinned data Dpre, may be transferred from the other radiographic image capturing devices P to the image generator C. The data in a state of mixture of the thinned data Dpre and the real signal values D* may be transferred to the image generator C from each of the radiographic image capturing devices P or the single radiographic image capturing device P in a case of moving type long image capturing.

The radiographic image capturing device P may store a predetermined thinning condition, and the thinned data Dpre may be extracted in accordance with the thinning condition. The thinning condition includes any of the thinning rate, thinning algorism and the bit number of data. The thinning condition of the thinned data Dpre may be transmitted to be specified from the console C (or image generator, hereinafter the same applies) to the radiographic image capturing device P, and may be stored in the radiographic image capturing device P when the thinning condition is transmitted.

As described above, communication can be made both in the wireless method and in the wired method between the radiographic image capturing device P and the console C (see the communicator 30, connector 27 and antenna 29 in FIG. 3). For example, the console C may apply a first thinning condition (thinning rate or the like) in a case where transferring is performed in the wired method, and the console C may apply a second thinning condition having smaller data amount of thinned data Dpre than the first thinning condition in a case where transferring is performed in the wireless method.

For example, the console C may monitor the transferring speed from the radiographic image capturing device P to the image generator C, and according to the transferring speed divided by one threshold value condition or more, the console C may perform control by switching the above thinning condition. The radiographic image capturing device P may monitor the transferring speed to the image generator C.

The console C may store the configuration of communication method (wireless method or wired method) from the radiographic image capturing device P to the image generator C and the transferring speed, for example, and apply the thinning condition corresponding to the transferring speed in the communication method in the past capturing which is same as the communication method in this capturing.

In this case, the image generator C generates the combined image ppre for check by using the thinned data Dpre which was extracted by a different thinning condition, and at that time, it is possible to obtain, from the console C, information on the thinning condition or the like under which the thinned data Dpre was extracted, and generate the combined image ppre for check by performing appropriate processing based on the obtained thinning condition to the thinned data Dpre and display the combined image ppre for check on the display Ca (see FIG. 1).

The present invention is not limited to the above embodiments, and modifications can be appropriately made within the scope of the present invention.

INDUSTRIAL APPLICABILITY

The present invention is applicable to the field (especially, medical field) in which the radiographic image capturing is performed.

EXPLANATION OF REFERENCE NUMERALS 7 radiation detector
22 controller (image generator)
50 radiographic image capturing system
C console (image generator)
Ca display
D signal value
Dpre, Dpre_raw, Dpre_cor thinned data
H subject
P, P1 to P3 radiographic image capturing device
p combined image, combined image for output
p1 to p3 radiographic image
ppre, ppre_raw, ppre_cor combined image for check
ppre_cor combined image for check generated later
ppre_raw combined image for check generated earlier
ppre_raw, ppre_cor a plurality of combined images for check which are processed differently

The invention claimed is:

1. A radiographic image capturing system comprising:
a plurality of radiographic image capturing devices which read signal values corresponding to doses of emitted radiation from a plurality of respective radiation detectors; and
a console which includes a display and a hardware processor that generates a plurality of radiographic images based on the signal values respectively read by the plurality of radiographic image capturing devices, and generates a combined image by combining the generated plurality of radiographic images, wherein
the plurality of radiographic image capturing devices simultaneously receive emission of radiation,
before the combined image for output is generated, the hardware processor generates a combined image for check by replacing processing among generation of the radiographic images, image processing to the radiographic images and generation of the combined image for output with simplified processing and performing the simplified processing, and after all signal values that are bases for generating the combined image for check among the signal values are received from the plurality of radiographic image capturing devices and the combined image for check is generated, the hardware processor causes the generated combined image for check to be displayed on the display.

2. The radiographic image capturing system according to claim 1, wherein the combined image is a combined image which is obtained by combining a plurality of radiographic images obtained by dividing a subject into a plurality of subjects and capturing the subjects.

3. The radiographic image capturing system according to claim 1, wherein the simplified processing is processing of generating the combined image for check by using thinned data which is extracted from the signal values read by the radiographic image capturing device.

4. The radiographic image capturing system according to claim 1, wherein the hardware processor generates a plurality of combined images for check which are processed differently, and the hardware processor causes the plurality of combined images for check to be displayed on the display in a generated order in such a manner that the combined image for check which is generated earlier is replaced with the combined image for check which is generated later.

5. The radiographic image capturing system according to claim 1, wherein the hardware processor causes the generated radiographic image to be displayed on the display until all the radiographic images necessary for generating the combined image for check are obtained.

6. The radiographic image capturing system according to claim 1, wherein, when the radiographic image is generated, in a case where a combinable radiographic image is generated, the hardware processor combines the radiographic images and causes the combined radiographic images to be displayed on the display.

7. The radiographic image capturing system according to claim 1, wherein the hardware processor is able to perform image editing to the combined image for check.

8. The radiographic image capturing system according to claim 7, wherein, when the combined image for output is generated, the hardware processor applies the image editing, which is performed to the combined image for check, to the generated combined image for output.

9. The radiographic image capturing system according to claim 1, wherein, in a case where failed image processing is performed based on the combined image for check, the hardware processor does not perform processing of combining the generated plurality of radiographic images, and does not perform processing of generating the combined image for output.

10. The radiographic image capturing system according to claim 9, wherein, in a case where the failed image processing is cancelled, the hardware processor restarts the processing of combining the generated plurality of radiographic images and generates the combined image for output.

11. The radiographic image capturing system according to claim 1, wherein, in a case where the combined image for check is approved, the hardware processor generates the combined image for output.

12. The radiographic image capturing system according to claim 1, wherein the radiographic image capturing device transmits thinned data extracted from the signal values to the hardware processor, and the hardware processor generates the combined image for check by using the received thinned data.

13. The radiographic image capturing system according to claim 1, wherein the radiographic image capturing device includes the hardware processor.

14. A method for generating and displaying a combined image for check, comprising the steps of:

in a console having a display and a hardware processor, generating, by the hardware processor, a plurality of radiographic images based on signal values read from a plurality of respective radiation detectors in a plurality of radiographic image capturing devices that simultaneously receiving emission of radiation, and combining, by the hardware processor, the generated plurality of radiographic images to generate a combined image for output;

before the combined image for output is generated, generating the combined image for check by replacing processing among generation of the radiographic images, image processing to the radiographic images and generation of a combined image with processing which is more simplified than processing performed when the combined image for output is generated, performing the simplified processing by the hardware processor to generate the combined image for check, and after all signal values that are bases for generating the combined image for check among the signal values are received from the plurality of radiographic image capturing devices and the combined image for check is generated, the hardware processor causing the generated combined image for check to be displayed on the display in the console.

* * * * *